United States Patent
Streng et al.

(10) Patent No.: US 7,345,073 B2
(45) Date of Patent: Mar. 18, 2008

(54) METHOD FOR TREATING CRYPTORCHIDISM

(75) Inventors: Tomi Streng, Turku (FI); Sari Mäkelä, Turku (FI); Risto Santti, Naantali (FI); Matti Poutanen, Turku (FI); Xiangdong Li, Turku (FI)

(73) Assignee: Hormos Medical Ltd., Turku (FI)

( * ) Notice: Subject to any disclaimer, the term of this patent is extended or adjusted under 35 U.S.C. 154(b) by 117 days.

(21) Appl. No.: 11/245,026

(22) Filed: Oct. 7, 2005

(65) Prior Publication Data

US 2006/0030570 A1 Feb. 9, 2006

Related U.S. Application Data

(63) Continuation of application No. 10/359,558, filed on Feb. 7, 2003, now abandoned.

(51) Int. Cl.
*A61K 31/41* (2006.01)
(52) U.S. Cl. .................................................. 514/383
(58) Field of Classification Search ................. 514/383
See application file for complete search history.

(56) References Cited

FOREIGN PATENT DOCUMENTS

| WO | WO 91/10444 A1 | 7/1991 |
|----|----------------|--------|
| WO | WO 94/13645 A1 | 6/1994 |

OTHER PUBLICATIONS

Li, X., et al., "Altered Structure and Function of Reproductive Organs in Transgenic Male Mice Overexpressing Human Aromatase," *Endocrinol.* 142:2435-2442 (2001).
Nef, S. et al., "A Molecular Basis for Estrogen-Induced Cryptorchidism," *Devel. Biol.* 224:354-361 (2000).
Abney, T., "The Potential Roles of Estrogens in Regulating Leydig Cell Development and Function: A Review," *Steroids* 64:610-617 (1999).

*Primary Examiner*—San-Ming Hui
(74) *Attorney, Agent, or Firm*—Rothwell, Figg, Ernst & Manbeck pc

(57) ABSTRACT

The present invention relates to a method and pharmaceutical composition for the treatment of male individuals suffering from cryptorchidism comprising administering to said individuals an effective amount of an aromatase inhibitor, preferably finrozole.

15 Claims, No Drawings

METHOD FOR TREATING CRYPTORCHIDISM

CROSS-REFERENCE TO RELATED APPLICATIONS

The present application is a continuation of U.S. patent application Ser. No. 10/359,558, filed 7 Feb. 2003, the application being incorporated by reference herein in its entirety.

FIELD OF THE INVENTION

This invention relates to a method for the treatment of cryptorchidism, i.e. testicular non-descendent in male individuals.

BACKGROUND OF THE INVENTION

The publications and other materials used herein to illuminate the background of the invention, and in particular, cases to provide additional details respecting the practice, are incorporated by reference.

Testicular descent occurs in two steps on the embryonic stage and the process is affected by several factors. Transabdominal descent begins after sexual differentiation at 8 to 10 weeks. The testis reaches the inguinal region at about the 15$^{th}$ week. The inguinal phase of testicular descent begins at 24-28 weeks when the testis rapidly passes through the inguinal canal and then more slowly arrives in the scrotum at 35-40 weeks (1).

The incidence of non-descended testis (in the following also called cryptorchidism, which term stands for failure of one or both of the testes to descend) has been 4.3% in all newborn male infants. At the age of three months the incidence is 1.0% and at the age of one year 0.8%. According to a recent English study, the incidence of non-descended testis has risen to 5.1% among newborns and 1.6% at the age of three months (2). Also in Denmark a growth of the incidence has been reported. Some of the increase may be attributed to the increased viability of very low birth weight infants, but even in full-term infants the incidence has risen to 4.1% at birth and 1.6% at three months (2). Excessive maternal exposure to estrogens such as diethylstilbestrol and to oral contraceptives has been suggested as an etiological factor associated with the increased incidence of cryptorchidism. Endogenous estrogens have also been suggested to be relevant to testicular non-descent. An increased risk of cryptorchidism and testicular cancer has been associated with elevated maternal estrogen consentrations during pregnancy (3). Overweight women that are nulliparous have lower SHBG levels, with a resulting higher bioavailability for estrogens. The increase in the amount of biologically active estrogens may extend during pregnancy and subsequently lead to a clinical condition that exposes the fetus to high estrogen levels (3). There is experimental evidence confirming the role of estrogens. Perinatal exposure of the mouse to either 17β-estradiol or diethylstilbestrol results in testicular abnormalities such as cryptorchidism, testicular hypoplasia, sperm abnormalities, epididymal cysts and testicular tumors (4 and 5).

Testicular maldescent may strongly influence male fertility even when treated and fertility is frequently impaired, particularly in cases of bilateral cryptorchidism. Testicular cancer is also associated with cryptorchidism.

One method for the treatment of cryptorchidism is surgery. Some decades ago, the surgery was carried out at the age of about 5-10 years. There has, however, been a stepwise decrease in the age at which surgery should be carried out, mainly due to histological evidence of testicular damage which occurs in untreated non-descended testis after infancy. At present, the operation is recommended before two years age.

Cryptorchidism has also be subjected to hormonal treatment with hCG (human chorionic gonadotrophin) or LHRH (lutenizing-hormone releasing hormone). During the last decades the success rate of hCG treatment has varied from 6 to 55%. The success rates achieved by using LHRH have been reported to vary between 9 and 78%. According to one study, both LHRH and hCG have been found to be ineffective in cases of true non-descended testes.

The known treatment methods are also related to risks. The most significant complication of surgery is vascular damage. Hormonal treatment may also have adverse effects on the testis. Inflammation-like reactions have been found in non-descended testes during the period immediately following hCG injections.

Thus, there is a great need for improved treatment methods of cryptorchidism.

SUMMARY OF THE INVENTION

The inventors of the present invention have surprisingly found that cryptorchidism can be successfully treated by administering an aromatase inhibitor.

Thus, this invention relates to a method for the treatment of male individuals suffering from cryptorchidism comprising administering to said individuals an effective amount of an aromatase inhibitor.

According to another aspect, this invention concerns the use of an aromatase inhibitor for the manufacture of a pharmaceutical composition useful for the treatment of male individuals suffering from cryptorchidism.

DETAILED DESCRIPTION OF THE INVENTION

Aromatase is an enzyme complex involving a NADPH-cytochrome C reductase and a specific cytochrome P-450 protein. The reaction which is catalyzed by aromatase is unique in the biosynthesis of steroids, as it involves conversion of ring A of the steroid structure to an aromatic ring with the loss of the angular C-19 methyl group and cis-elimination of the 1β and 2β hydrogens to yield estrogen and formic acid. Aromatization is the last and critical step in the biosynthesis of estrogens from cholesterol. Therefore, specific blockade of this enzyme does not cause deprivation of other essential steroids such as cortisol or male sex hormones.

As suitable selective aromatase inhibitors can be mentioned, for example, the compounds covered by formula (I)

in International patent application publication No. WO 94/13645. Said compounds (I)

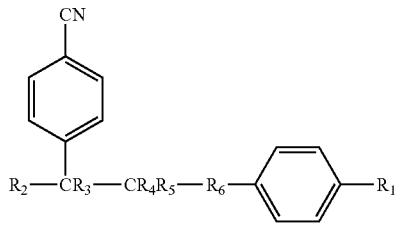

include members wherein $R_1$ is hydrogen, methyl, methoxy, nitro, amino, cyano, trifluoromethyl, difluoromethyl, monofluoromethyl or halogen; $R_2$ is a heterocyclic radical selected from 1-imidazolyl, triazolyl, tetrazolyl, pyrazolyl, pyrimidinyl, oxazolyl, thiazolyl, isoxazolyl and isothiazolyl; $R_3$ is hydrogen or hydroxy; $R_4$ is hydrogen; $R_5$ is hydrogen or hydroxy; or $R_4$ is hydrogen and $R_3$ and $R_5$ combined form a bond; or $R_3$ is hydrogen and $R_4$ and $R_5$ combined form =O; $R_6$ is methylene, ethylene, —CHOH—, —CH$_2$CHOH—, —CHOH—CH$_2$—, —CH=CH— or C(=O)—; $R_4$ is hydrogen and $R_5$ and $R_6$ combined is =CH— or =CH—CH$_2$—; or a stereoisomer, or a non-toxic pharmaceutically acceptable acid addition salt thereof.

A preferred compound of this group 1-[1-(4-cyanophenyl)-3-(4-fluorophenyl)-2-hydroxypropyl]-1,2,4-triazole. Particularly preferred is the compound 1-[1-(4-cyanophenyl)-3-(4-fluorophenyl)-2-hydroxypropyl]-1,2,4-triazole, diasteroisomer a+d, which also is known under the generic name finrozole. The separated a and d isomers of this diastereomer mixture are also preferred.

As examples of other suitable aromatase inhibitors can be mentioned anastrozole, fadrozole, letrozole, vorozole, roglethimide, atamestane, exemestane, formestane, YM-511 (4-[N-(4-bromobenzyl)-N-(4-cyanophenyl)amino]-4H-1,2,4-triazole), ZD-1033 (anastrozole) and NKS-01 (14-α-hydroxyandrost-4-ene-3,6,17-trione) and their stereoisomers and non-toxic pharmaceutically acceptable acid addition salts.

Finrozole, like all presently described specific aromatase inhibitors, have been intended mainly for the treatment of female breast cancer where estrogens stimulate the tumor growth, and aromatase inhibitor, by depleting estrogens, inhibits the tumor growth. In men aromatase inhibitors dramatically decrease estradiol concentrations and may simultaneously increase the testosterone concentrations being thus especially beneficial for the increasing the decreased androgen to estrogen ratio (DATER) and for the treatment of voiding dysfunction which are due to the DATER, as described in WO 94/13645.

For the purpose of this invention, the aromatase inhibitor or its stereoisomer or pharmaceutically acceptable salt can be administered by various routes. The suitable administration forms include, for example, oral formulations; parenteral injections including intravenous, intramuscular, intradermal and subcutaneous injections; and transdermal or rectal formulations. Suitable oral formulations include e.g. conventional or slow-release tablets and gelatine capsules, and especially liquid mixtures.

The required dosage of the aromatase inhibitor compounds will vary with the particular condition being treated, the severity of the condition, the duration of the treatment, the administration route and the specific compound being employed. Generally, the treatment should last from days to a few months and should be stopped as soon as the testes have descended. For example, finrozole can be administered perorally preferentially once daily. The daily dose is 0.1-1 mg/kg body weight, preferably 0.2-0.6 mg/kg body weight. Finrozole can be given as tablets or other formulations like gelatine capsules alone or mixed in any clinically acceptable non-active ingredients which are used in the pharmaceutical industry.

Preferably, the aromatase inhibitor should be administered to boys before the puberty. Most preferably, the treatment should take place on boys in the age of 1 to 5 years.

The invention will be illuminated by the following non-restrictive Experimental Section.

Experimental Section

Androgens and estrogens play a central role in organization and differentiation of the developing endocrine system in general and of the peripheral reproductive tract in particular. Although, estrogen is considered to be the female sex steroid, and androgen that of the male, there is considerable amount of overlap in activities of the two groups of steroids between the sexes. Thus, the differences between the two sexes in their response to estrogens and androgens are not qualitative but merely due to quantitative variation in sex steroid concentrations, and the balance between androgen and estrogen action. Both estrogens and androgens exert their biological action via specific nuclear receptors, and in addition to the cell specific expression of the receptors the sex steroid concentrations in target cells determine the extent of steroid action. Androgens can be converted into estrogens via an enzymatic reaction catalyzed by the enzyme complex called P450 aromatase.

Aromatization of androgens is the key step in estrogen production, and in regulation of the delicate balance between estrogens and androgens in gonads and sex steroid target tissues.

Test and Control Compounds

The aromatase inhibitor finrozole {MPV-2213ad (10695U, without purification, Hormos Medical Ltd.} was the test compound. Vehicle (CMC-solution) was used as control substance. CMC-solution was prepared as follows: 0.25 g carboxylmethylcellulosa (CMC) (lot. 939512, Tamro OYJ) was weighed and solubilized in 50 ml of deionized (Milli-Q) water. The solution was prepared once a week and stored at +4° C. The dose level of finrozole 10 mg/kg dose level was used. The vehicle-test/control-solution, which was given to the test animals, was prepared daily as follows: the appropriate amount of finrozole was weighed in a transparent glass mortar. A few drops of vehicle were added and the mixture was thoroughly mixed. After this ⅓ of the final volume of vehicle was added to the mortar and placed into an ultrasonic incubator for five minutes. This procedure was done total of three times to reach the final volume.

Test Animals

Aromatase over expressing mice AROM+ (line 021) were used in this study. The mice were maintained under standard laboratory conditions at 12:12 light/dark cycle, and received free access to soyfree pelleted food (SDS, Witham, Essex, UK), and tap water.

We have generated a transgenic mouse model bearing the human ubiquitin C promoter/human P450 aromatase fusion gene (AROM+). The AROM+ male mice produced are characterized by an imbalance in sex hormone metabolism, resulting in serum estradiol concentrations typical for females, combined with significantly reduced testosterone level. The AROM+ males present with a multitude of severe structural and functional abnormalities of the reproductive system, such as cryptochidism, dysmorphic semiferous tubules and disrupted spermatogenesis. The males also have small or rudimentary accessory sex glands with abnormal morphology, a prominent prostatic utricle with squamous epithelial metaplasia, and abnormal morphology of ejaculatory duct and vas deferens. In addition, the abdominal wall muscle layer is thin, and the adrenals are enlarged with cortical hyperplasia. Some of these abnormalities, such as undescended testes and undeveloped seminal vesicles resemble those observed in animals exposed to high estrogen levels in perinatal life (3 and 4), indicating that the elevated aromatase activity resulted in excessive estrogen exposure also during early phase of development. Some of the disorders in reproductive system, furthenmore, can be explained by the fact that the AROM+ males are hypoandrogenic. The AROM+ mouse model provides a useful tool to investigate the consequences of prolonged imbalance in the androgen-estrogen ratio, and in particular, of excessive estrogen exposure on male reproductive functions.

In AROM+ males, the seminal vesicles, testes and prostate lobes were significantly reduced in size. All the AROM+ males were cryptorchid, with the testis located in the abdominal cavity. The cryptorchid testes were significantly smaller than the wild type in size, as were the epididymides. Microscopically, the diameter of the seminiferous tubule of the AROM+ mice was smaller and the lumen was larger than those of the wild type were. In the seminiferous epithelium, there were no germ cells beyond the stage of pachytene. Numerous degenerating germ cells could be seen near the lumen, which showed less intensively stained nuclei, homogeneously pink-stained cytoplasm. Numerous vacuoles of different sizes were observed within the epithelium and interstitium. The number of interstitial cells per $mm^2$ was also increased in the AROM+ mice than the wild type.

Two of the five AROM+ founder mice generated (one male, number 33 and one female, number 21) were fertile and they were used to generate subsequent generations by breeding with the wt FVB/N mouse background. All the male mice born of both lines (from F1 generation and thereafter) were infertile, and hence, the transgenic lines could be established only by mating the AROM+ females with wild type FVB/N males.

In the experiment there was six different kind of groups of male mice, ten animals in each group. One control group (wild type FVB/N) received vehicle, as well as the other control (021 line) group. The last groups were treated with finrozole (10 mg/kg).

Administration of the Compounds

The dosing (4 ml solution/kg) of the animals took place p.o. daily for six weeks. On Saturdays, however, double dose of the test compounds was given to animals. On sundays there was no treatment.

Results

The trial was conducted in total of 39 mice. The possible undescended testes were palpated and also examined by opening the animal. The palpation was conducted as follows: the abdominal area of the animal was pressed gently and simultaneously the fingers were dragged towards the scrotum. If the testes are able to descend, they appear into the scrotum, and if not the testes are undescended. The results are shown in Table 1. The relative weights (testes weight/animal weight) are shown in Table 2.

TABLE 1

Number of Descended or Undescended Testes

| Testes | Number of descended testes | Number of undescended testes | Number of partly descended testes |
|---|---|---|---|
| Wild type (FVB/N) vehicle group (ten mice) | 20 | | |
| Wild type finrozole group (nine mice) | 18 | | |
| AROM+ (021) vehicle group (ten mice) | | 20 | |
| AROM+ (021) finrozole group (ten mice) | 17 | 1 | 2 |

TABLE 2

Relative Testes Weights (Testes Weight/Animal Weight) in Vehicle and Finrozole Treatment Groups in Wild Type and AROM+ 021 Groups (N.S = Non-Significant. A = ANOVA and M = Mann-Whitney U-test)

| | Relative testes weights | P-value compared to wild type vehicle group | P-value compared between vehicle and treatment |
|---|---|---|---|
| Wild type (FVB/N) vehicle group (n = 10) | 0.0027 (SD 0.0002) | | |
| Wild type finrozole group (n = 7) | 0.0027 (SD 0.0003) | N.S (A) | N.S (A) |
| AROM+ (021) vehicle group (n = 10) | 0.0017 (SD 0.0006) | 0.002 (M) | |
| AROM+ (021) finrozole group (n = 10) | 0.0033 (SD 0.0003) | N.S (A) | 0.0007 (M) |

N.S = Non-Significant
A = ANOVA
M = Mann-Whitney U-test)

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

1. Taskinen, Seppo: "Clinical outcome after treatment of undescended testes". Thesis. University of Helsinki 1997.
2. John Radcliffe Hospital Cryptorchidism Study Group: "Cryptorchidism: a prospective study of 7500 consecutive male births, 1984-8. Arch Dis Child 67:892-899, 1992.
3. Bernstein L, Pike M C, Depue R H, Ross R K, Moore J W, Henderson B E: Maternal hormone levels in early gestation of cryptorchid males: A case-control study. Br J Cancer 58:379-381, 1988.
4. McLachan J A: Rodent models for perinatal exposure to diethylstilbestrol and their relation to human disease in the male. In Herbst A L, Bern H A (eds.): "Developmental Effects of Diethylstilbestrol (DES) in Pregnancy." New York, N.Y.: ThiemeStratton Inc., 1981, pp 148-157.

5. Newbold R R, Bullock B C, McLachan J A: Adenocarsinoma of the rete testis. Diethylstilbestrol-induced lesions of the mouse rete testis. Am J Pathol 125:625-628 1986.

The invention claimed is:

1. A method for the treatment of a male individual suffering from cryptorchidism comprising administering to the individual a therapeutically effective amount of an aromatase inhibitor, wherein the aromatase inhibitor is a compound of selected from the group consisting of anastrozole, fadrozole, letrozole, vorozole, roglethimide, atamestane, exemestane, formestane, YM-511 (4-[-(4-bromobenzyl)-N-(4-cyanophenyl)amino]-4H-1,2,4-triazole), ZD-1033 (anastrozole) and NKS-01 (14-α-hydroxyandrost-4-ene-3,6,17-trione); or a compound of formula (I)

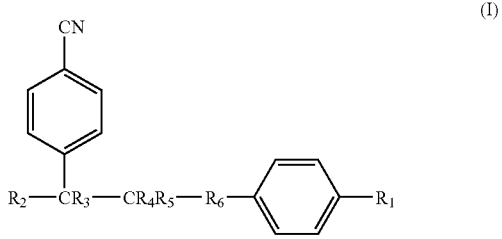

wherein $R_1$ is hydrogen, methyl, methoxy, nitro, amino, cyano, trifluoromethyl, difluoromethyl, monofluoromethyl or halogen;
$R_2$ is a heterocyclic radical selected from 1-imidazolyl, triazolyl, tetrazolyl, pyrazolyl, pyrimidinyl, oxazolyl, thiazolyl, isoxazolyl and isothiazolyl;
$R_3$ is hydrogen or hydroxy;
$R_4$ is hydrogen;
$R_5$ is hydrogen or hydroxy, or $R_3$ and $R_5$ taken together are a bond, or $R_4$ and $R_5$ taken together are =O when $R_3$ is hydrogen;
$R_6$ is methylene, ethylene, —CHOH—, —CH$_2$CHOH—, —CHOH—CH$_2$—, —CH=CH— or —C(=O)—, or $R_5$ and $R_6$ taken together are =CH— or =CH—CH$_2$—;
or a stereoisomer, or a non-toxic pharmaceutically acceptable acid addition salt thereof, or a mixture thereof.

2. The method according to claim 1, wherein the aromatase inhibiting compound is 1-[1-(4-cyanophenyl)-3-(4-fluorophenyl)-2-hydroxypropyl]-1,2,4-triazole, a stereoisomer thereof or a non-toxic pharmaceutically acceptable acid addition salt thereof, or a mixture thereof.

3. The method according to claim 2, wherein the aromatase inhibiting compound is 1-[1-(4-cyanophenyl)-3-(4-fluorophenyl)-2-hydroxypropyl]-1,2,4-triazole, diasteroisomer a+d, the separated isomer a or the separated isomer d.

4. The method according to claim 1, wherein the aromatase inhibitor is administered to the individual before the puberty.

5. The method of claim 4 wherein the aromatase inhibitor is administered to the individual at an age between 1 and 5 years old.

6. The method according to claim 2, wherein the aromatase inhibitor is administered to the individual before the puberty.

7. The method of claim 6, wherein the aromatase inhibitor is administered to the individual at an age between 1 and 5 years old.

8. The method according to claim 3, wherein the aromatase inhibitor is administered to the individual before the puberty.

9. The method of claim 8, wherein the aromatase inhibitor is administered to the individual at an age between 1 and 5 years old.

10. The method of claim 1, wherein the aromatase inhibitor is administered in an amount between 0.1 mg/kg and 1.0 mg/kg.

11. The method of claim 10, wherein the aromatase inhibitor is administered in an amount of between 0.2 mg/kg and 0.6 mg/kg.

12. The method of claim 2, wherein the aromatase inhibitor is administered in an amount between 0.1 mg/kg and 1.0 mg/kg.

13. The method of claim 12, wherein the aromatase inhibitor is administered in an amount between 0.2 mg/kg and 0.6 mg/kg.

14. The method of claim 3, wherein the aromatase inhibitor is administered in an amount between 0.1 mg/kg and 1.0 mg/kg.

15. The method of claim 14, wherein the aromatase inhibitor is administered in an amount between 0.2 mg/kg and 0.6 mg/kg.

* * * * *